United States Patent
Curry

(10) Patent No.: US 8,065,796 B2
(45) Date of Patent: Nov. 29, 2011

(54) METHOD AND APPARATUS FOR USING FLEX CIRCUIT TECHNOLOGY TO CREATE AN ELECTRODE

(75) Inventor: Kenneth M. Curry, Oceanside, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1228 days.

(21) Appl. No.: 11/709,635

(22) Filed: Feb. 22, 2007

(65) Prior Publication Data

US 2007/0200254 A1 Aug. 30, 2007

Related U.S. Application Data

(60) Provisional application No. 60/777,135, filed on Feb. 27, 2006.

(51) Int. Cl.
*H01K 3/00* (2006.01)
(52) U.S. Cl. .......................... 29/849; 174/261
(58) Field of Classification Search .................. 174/261; 29/849

See application file for complete search history.

(56) References Cited

U.S. PATENT DOCUMENTS

| | | | |
|---|---|---|---|
| 4,542,291 A | 9/1985 | Zimmerman | |
| 4,937,444 A | 6/1990 | Zimmerman | |
| 5,423,883 A | 6/1995 | Helland | |
| 5,838,546 A | 11/1998 | Miyoshi | |
| 5,914,179 A | 6/1999 | Inaba | |
| 5,987,361 A | 11/1999 | Mortimer | |
| 6,020,561 A * | 2/2000 | Ishida et al. | 174/261 |
| 6,833,612 B2 | 12/2004 | Kinsman | |
| 6,885,107 B2 | 4/2005 | Kinsman | |
| 6,940,141 B2 | 9/2005 | Kinsman | |
| 6,956,295 B2 | 10/2005 | Kinsman | |
| 6,964,886 B2 | 11/2005 | Kinsman | |
| 6,972,423 B2 | 12/2005 | Welland et al. | |
| 6,985,764 B2 | 1/2006 | Mason et al. | |
| 7,122,390 B2 | 10/2006 | Kinsman | |
| 2004/0183213 A1 | 9/2004 | Hsu | |
| 2006/0180245 A1* | 8/2006 | Wicker et al. | 148/23 |

FOREIGN PATENT DOCUMENTS

| | | |
|---|---|---|
| EP | 0 351 851 | 1/1990 |
| WO | WO-02/102224 | 12/2002 |

OTHER PUBLICATIONS

European Search Report, Oct. 30, 2009.
International Search Report for Patent Application No. PCT/US2007/004472, Feb. 26, 2008.

* cited by examiner

*Primary Examiner* — Jeremy Norris
(74) *Attorney, Agent, or Firm* — Michael Crapenhoft

(57) ABSTRACT

A method of creating an active electrode that may include providing a flex circuit having an electrode made of a first material and providing a first mask over the flex circuit, the first mask having an offset region and an opening that exposes the electrode. The method may also include depositing a second material over the offset region and the opening, the second material being different from the first material and providing a second mask over the second material, the second mask having an opening over a portion of the second material that is over the offset region.

5 Claims, 7 Drawing Sheets

METHOD AND APPARATUS FOR USING FLEX CIRCUIT TECHNOLOGY TO CREATE AN ELECTRODE

CLAIM OF PRIORITY UNDER 35 U.S.C. §119

The present Application for Patent claims priority to Provisional Application No. 60/777,135 filed Feb. 27, 2006, and assigned to the assignee hereof and hereby expressly incorporated by reference herein.

FIELD OF THE INVENTION

The invention relates generally to flex circuit technology. More specifically, the invention relates to using flex circuit technology to create an electrode.

BACKGROUND

Flex circuits have been used in the micro-electronics industry for many years. In recent years, flex circuits have been used to design microelectrodes for in vivo applications. One flex circuit design involves a laminate of a conductive foil (e.g., copper) on a flexible dielectric substrate (e.g., polyimide). The flex circuit is formed on the conductive foil using masking and photolithography techniques. Flex circuits are desirable due to their low manufacturing cost, ease in design integration, and flexibility in motion applications.

SUMMARY

The invention relates to a method of creating an active electrode that may include providing a flex circuit having an electrode made of a first material and providing a first mask over the flex circuit, the first mask having an offset region and an opening that exposes the electrode. The method may also include depositing a second material over the offset region and the opening, the second material being different from the first material and providing a second mask over the second material, the second mask having an opening over a portion of the second material that is over the offset region.

The invention relates to an electrode that may include a substrate having a conductive trace made of a first material, and a first mask positioned over the conductive trace, the first mask having a first opening over a portion of the conductive trace. The electrode may also include a material of interest made of a second material and positioned over a portion of the conductive trace and over a portion of the first mask and a second mask over the material of interest, the second mask having a second opening over a portion of the material of interest, the second opening being offset from the first opening.

BRIEF DESCRIPTION OF THE DRAWINGS

The features, objects, and advantages of the invention will become more apparent from the detailed description set forth below when taken in conjunction with the drawings, wherein.

DETAILED DESCRIPTION

The invention is directed toward using a flex circuit to create an active electrode. The flex circuit has a copper trace that is masked and imaged onto a polyimide substrate. Flex circuits with copper traces have a low manufacturing cost. The end of the copper trace may be plated with a first material of interest (e.g., gold). A first mask is used to create an opening for an active electrode. A second material of interest (e.g., graphite and/or platinum) may be deposited or screen-printed into the opening and on an offset region. A second mask is used to cover the second material of interest that is over the opening. A membrane may be placed over the offset region to form the active electrode. The second material of interest over the offset region acts as a diffusion barrier to prevent, for example, electrolytes from coming into contact with the copper trace. The offset region prevents the copper trace from oxidizing at a positive potential, such as would be the case for a glucose electrode measuring peroxide vs. silver-silver chloride for example.

Figure 1:
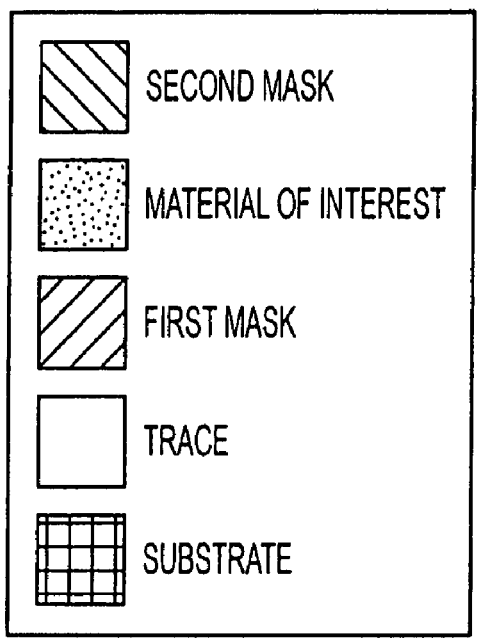
FIG. 1 is a cross-section view of an active electrode that is created using a flex circuit according to an embodiment of the invention.
Figure 1:
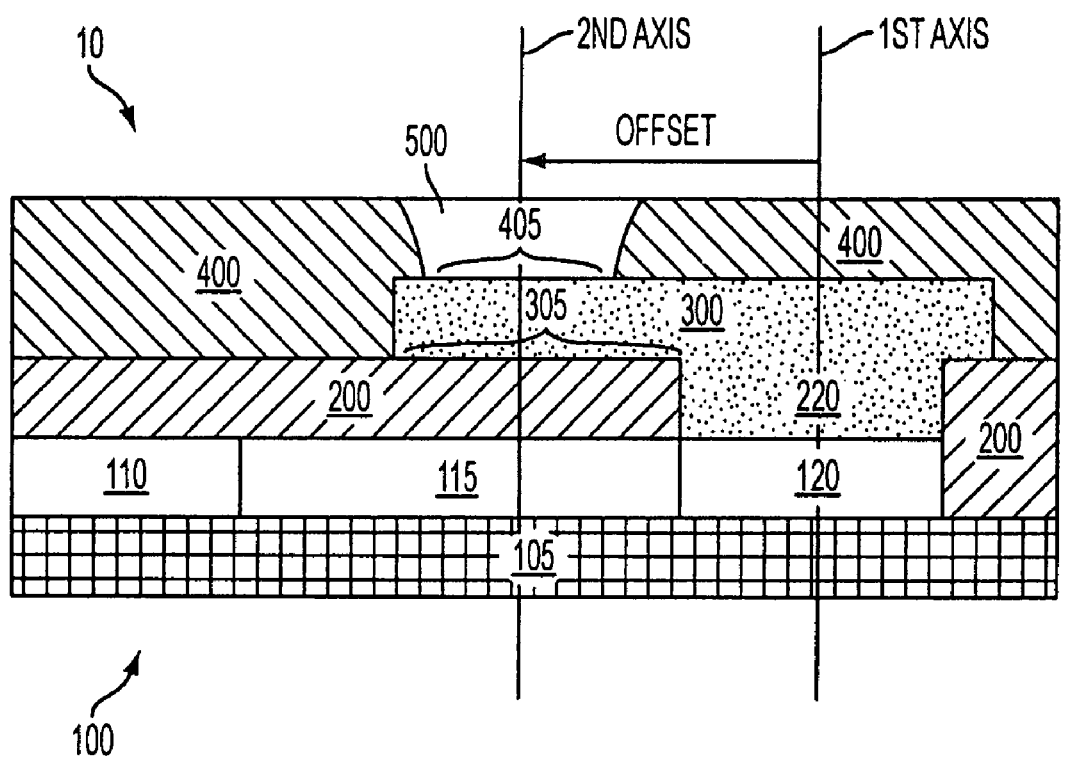
Figure 6A:
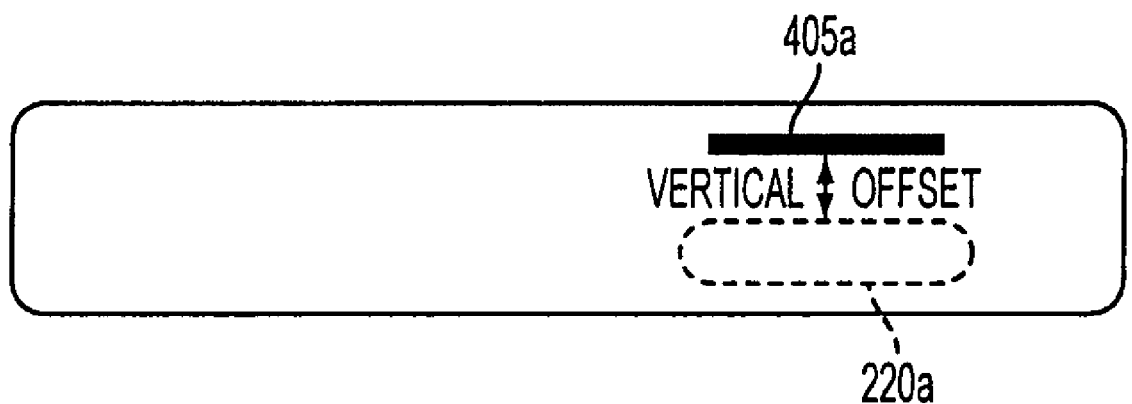
FIGS. 6A and 6B are top views showing vertical and horizontal offsets according to various embodiments of the invention.
Figure 6B:
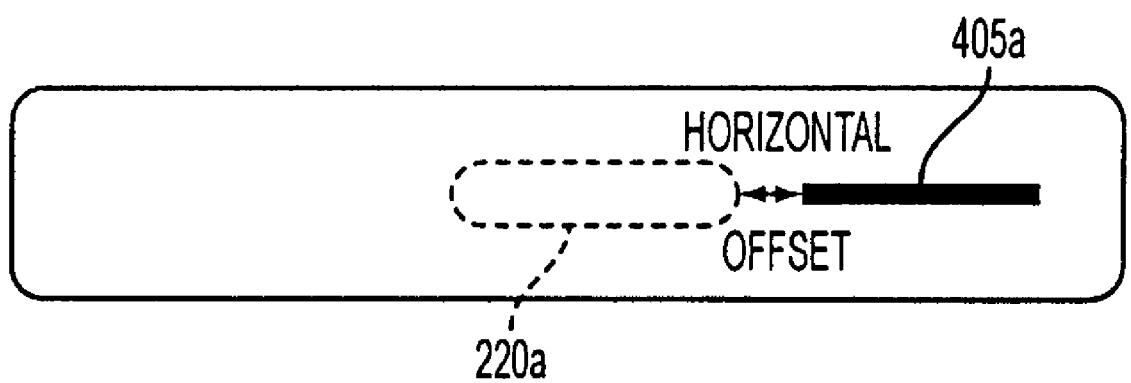
Figure 7:
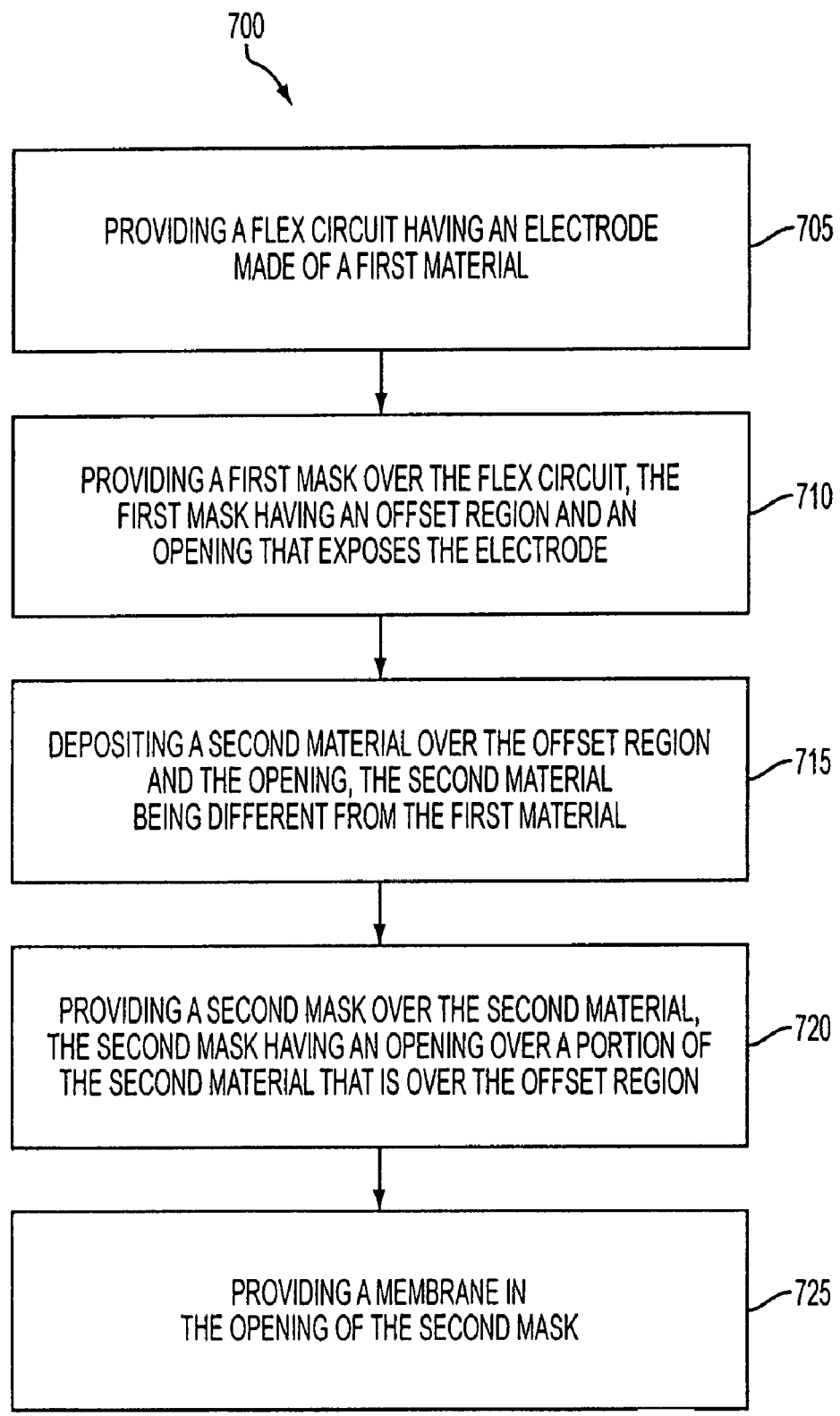
FIG. 7 is a flow chart showing a method of creating the electrode of FIG. 1 according to an embodiment of the invention.

FIG. 1 is a cross-section view of an active electrode 10 that is created using a flex circuit 100 according to an embodiment of the invention. The flex circuit 100 may include a substrate 105, one or more contacts 110, one or more traces 115, and one or more electrodes 120 (705). For illustrative purposes, the contacts 110, the traces 115, and the electrodes 120 are shown as different elements; however, the contacts 110, the traces 115, and the electrodes 120 may be collectively referred to as traces and may be formed using the same material (e.g., copper). The contacts 110, traces 115 and electrodes 120 are masked and imaged onto the substrate 105. A mask 200 is placed over the flex circuit 100 (710). The mask 200 may have an opening 220 that expose the electrodes 120 and that receive a material of interest 300, which is used to form the active electrode 10 (715). The material of interest 300 is also deposited over the mask 200 in an offset region 305. The offset region 305 is shown to be adjacent to the opening 220. A mask 400 having an opening 405 is deposited over the material of interest 300 (720). The opening 405 is located above the offset region 305 and is used for placement of a membrane 500 (725). The opening 220 is positioned along a first axis or plane and the opening 405 is positioned along a second axis or plane. The first axis or plane is not coincident with the second axis or plane. Hence, the first axis or plane is vertically and/or horizontally offset from the second axis or plane. FIGS. 1 and 6B show a horizontal offset and FIG. 6A shows a vertical offset. The horizontal offset may be along the length of the substrate 105 and the vertical offset may be along the width of the substrate 105. The mask 200 and/or the material of interest 300 may act as a diffusion barrier to prevent electrolytes coming in from the membrane 500 from contacting the electrodes 120. The offset region 305 prevents the electrodes 120 from undesirable electrochemical activity.

Figure 2:
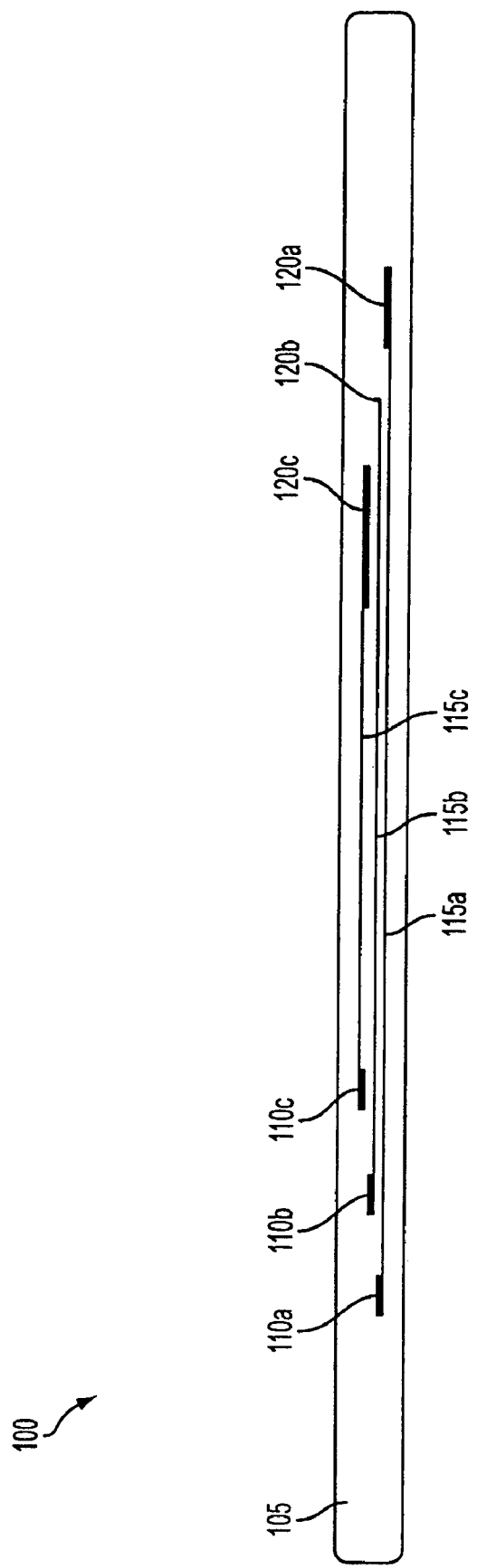
FIG. 2 is a top view of a flex circuit according to an embodiment of the invention.

FIG. 2 is a top view of a flex circuit 100 according to an embodiment of the invention. The contacts 110, the traces 115, and the electrodes 120 are made of a copper material and are formed on the substrate 105 using masking and photolithography techniques. The substrate 105 may be a flexible dielectric substrate such as a polyimide. The contacts 110 are used to connect to measurement devices such as a potentiostat. The traces 115 are used to carry voltage or current from the electrodes 120 to the contacts 110. As an example, FIG. 1 shows the flex circuit 100 having the substrate 105, three contacts 110a-c, three traces 115a-c, and three electrodes 120a-c.

Figure 3:
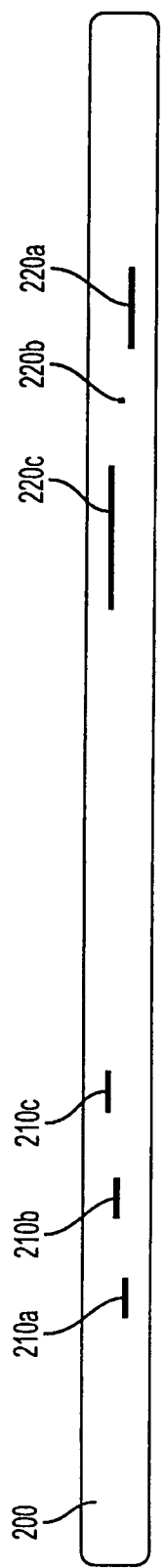
FIG. 3 is a top view of a mask that is used to cover the flex circuit of FIG. 1 according to an embodiment of the invention.

FIG. 3 is a top view of a mask 200 that is used to cover the flex circuit 100 shown in FIG. 2 according to an embodiment of the invention. The mask 200 may be made of a dielectric material such as a photoimagable epoxy or an ultraviolet curable epoxy material. The mask 200 has openings 210a-c and 220a-c. In one embodiment, the mask 200 covers the entire top surface of the flex circuit 100 except for areas that are above the contacts 110 and/or the electrodes 120. Hence, the openings 210a-c are positioned directly above the contacts 110a-c so that the contacts 110a-c are exposed through the openings 210a-c of the mask 200. Similarly, the openings 220a-c are located directly above the electrodes 120a-c so that the electrodes 120a-c are exposed through the openings 220a-c of the mask 200. Conventional lithography techniques may be used to deposit or place the mask 200 on the flex circuit 100.

Figure 4:
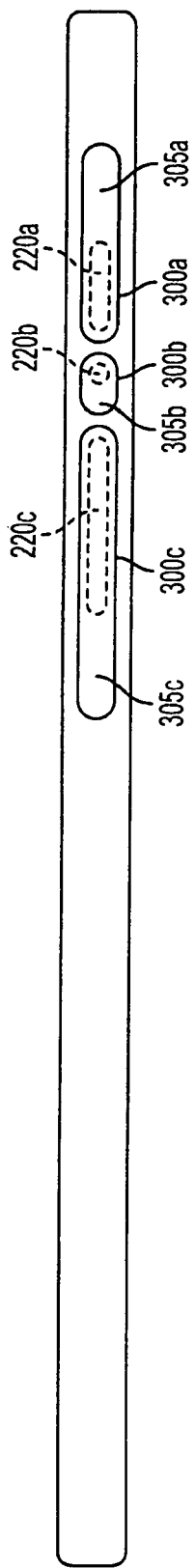
FIG. 4 is a top view showing one or more materials of interest deposited into and above the openings in the mask according to an embodiment of the invention.

FIG. 4 is a top view showing one or more materials of interest 300a-c deposited into and above the openings 220a-c in the mask 200 according to an embodiment of the invention. The materials of interest 300a-c provide a working surface for the electrodes 120a-c. The same material of interest 300 or different materials of interest 300 may be deposited over each of the openings 220a-c. The materials of interest 300 may be an ink or material made of carbon, gold, graphite, platinum, silver-silver chloride, rodium, palladium, other metals, and other materials having specific electrochemical properties. As an example, a platinum ink or material may be deposited over the openings 220a and 220c and a silver-silver chloride ink or material may be deposited over the opening 220b. The one or more materials of interest 300 may also be deposited over offset regions 305a-c that are adjacent to the openings 220a-c but are not directly over the openings 220a-c. The size of the offset regions 305a-c may vary depending on the particular application and the arrangement and configuration of the electrodes 120a-c. In one embodiment, the sizes of the offset regions 305a-c are about 0.010 inches, 0.003 inches and 0.050 inches, respectively.

Figure 5:
FIG. 5 is a top view of a mask that is used to cover the material of interest shown in FIG. 4 according to an embodiment of the invention.

FIG. 5 is a top view of the mask 400 that is used to cover the material of interest 300 shown in FIG. 4 according to an embodiment of the invention. The mask 400 may be made of a dielectric material such as a photoimagable epoxy or an ultraviolet curable epoxy material. The mask 400 has an opening 405 located above the offset region 305. In one embodiment, the mask 400 covers the entire top surface of the materials of interest 300 except for an area that is above the offset region 305. Hence, the opening 405 may be positioned directly above the material of interest 300, which is directly above the offset region 305. Conventional lithography techniques may be used to deposit or place the mask 400 on the material of interest 300.

Referring back to FIG. 1, a membrane 500 is deposited in the opening 405 and on the material of interest 300 (i.e., a working surface) to act as a sensing region. The membrane 500 may contain, for example, a glucose oxidase enzyme. The membrane 500 may allow molecules to pass at a certain rate so the material of interest 300 can accurately measure, for example, the glucose level in blood. That is, molecules in the blood can pass through the membrane 500 at a certain rate to the material of interest 300 for a specific measurement of the glucose in the blood. The membrane 500 and/or the material of interest 300 may be suitable for immersion into a fluid or solution containing species of interest (e.g., blood) and/or electrolyte. The contacts 110, the traces 115, and/or the electrodes 120 may not be suitable for immersion into a fluid or solution containing species of interest and therefore should be protected by a suitable encapsulant with appropriate dielectric properties.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

What is claimed is:

1. A method of creating an electrode, comprising:
    providing a substrate having a conductive trace thereon;
    applying a first mask over the conductive trace, the first mask having a first opening over a portion of the conductive trace;
    applying a material of interest over a portion of the conductive trace and over a portion of the first mask;
    applying a second mask over the material of interest, the second mask having a second opening over a portion of the material of interest, the second opening being offset from the first opening; and
    applying a membrane material into the second opening over the material of interest, wherein the membrane is of a material that allows molecules to pass at a controlled rate through the second opening to the material of interest.

2. The method of claim 1, wherein the conductive trace is made of a copper material and the material of interest is made of a material that is not copper.

3. The method of claim 1, wherein the first opening is positioned along a first axis and the second opening is positioned along a second axis that is not coincident with the first axis.

4. The method of claim 1, wherein the first opening is positioned along a first plane and the second opening is positioned along a second plane that is not coincident with the first plane.

5. The method of claim 1, wherein the conductive trace is made of a copper material and the material of interest is selected from a group consisting of a carbon, gold, graphite, platinum, silver-silver chloride, rhodium, and palladium material.

* * * * *